United States Patent [19]

Quarfoot

[11] Patent Number: 4,539,200

[45] Date of Patent: Sep. 3, 1985

[54] TREATMENT OF SKIN LESIONS

[75] Inventor: Alan Quarfoot, Palatine, Ill.

[73] Assignee: The Kendall Company, Boston, Mass.

[21] Appl. No.: 548,876

[22] Filed: Nov. 4, 1983

[51] Int. Cl.$^3$ .................... A61K 31/78; A61K 31/74
[52] U.S. Cl. ........................................ 424/81; 424/78
[58] Field of Search ................................. 424/81, 78

[56] References Cited

U.S. PATENT DOCUMENTS

| | | | |
|---|---|---|---|
| 3,579,628 | 5/1971 | Gander et al. | 424/81 |
| 4,062,831 | 12/1977 | Kopecer et al. | 424/81 |
| 4,225,580 | 9/1980 | Rothman et al. | 424/78 |
| 4,272,518 | 6/1981 | Moro et al. | 424/81 |

*Primary Examiner*—Elbert L. Roberts
*Assistant Examiner*—Freda L. Abramson

[57] ABSTRACT

Method and composition for cleansing wounds and skin burns or lesions by application of particles of cross-linked polymers of acrylamide, methacrylamide, ethacrylamide, and N-hydrocarbon substituted derivatives thereof.

5 Claims, No Drawings

TREATMENT OF SKIN LESIONS

This invention relates to a method and composition for cleansing wounds and skin burns and lesions by the application thereto of solid particles of a cross-linked polymer containing polymer units of the structure

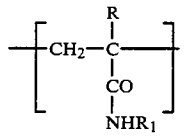

in which R is hydrogen, methyl or ethyl and $R_1$ is hydrogen, alkyl having 1 to 6 carbon atoms, or phenyl. Both homopolymers containing such polymer units and copolymers containing two or more specifically different such units are included.

It has previously been proposed to cleanse wounds by the application thereto of dry polymer particles of cross-linked carbohydrate or sugar alcohol polymers as described in Rothman et al U.S. Pat. No. 4,225,580. However, such particles have limited capacity to absorb serum or pus and limited capacity to absorb proteins, necessitating frequent changes in order to maintain effective cleansing.

It has now been found that wound cleansing material in the form of dry solid particles of a cross-linked polymer having the following composition

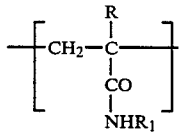

in which R is hydrogen, methyl or ethyl and $R_1$ is hydrogen, alkyl having 1 to 6 carbon atoms, or phenyl, has very high capacity for absorption of serum, pus and other fluids as well as proteins found therein and is highly effective in promoting healing of wounds and skin lesions. The wound cleansing material is consequently useful for the treatment of such diverse clinical conditions as severe hand burns, sacral and leg ulcers, non-venereal penile ulcers, herpes simplex and herpes zoster lesions, surgical incisions such as those resulting from hemorrhoidectomy, fistulectomy, and cryosurgery for cutaneous malignancies. Particularly preferred are those cross-linked polymers or copolymers in which R and $R_1$ together contain at least one carbon atom, that is, those in which R is methyl or ethyl or those in which $R_1$ is alkyl or phenyl as well as those in which both R and $R_1$ contain at least one carbon atom. The preferred materials, in which R and $R_1$ together contain at least one carbon atom, become bright white even when wetted with whole blood or hemolyzed serum. They consequently are highly visible after application to a wound, a property which facilitates their being flushed from the wound.

The size of the polymer particles of the present invention is not critical and may vary over a wide range up to about 0.5 mm. in diameter, preferably from 0.1 to 0.3 mm. in diameter.

The polymer may be prepared and cross-linked by any conventional procedure. In a preferred embodiment the desired monomer or monomers, each having the composition:

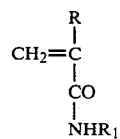

in which R and $R_1$ have the meanings defined above are subjected to solution polymerization in the presence of a suitable catalyst or initiator to form a polymer gel which is then sub-divided or granulated and dried, after which it may be ground to the desired particle size if necessary.

Among the monomeric materials having the required composition which may be employed in the present invention are acrylamide, methacrylamide, ethacrylamide, N-methylacrylamide, N-isopropylacrylamide, N-tert.-butylacrylamide, N-phenylacrylamide. Any conventional cross-linking agent capable of producing water-insoluble covalently cross-linked polymers may be employed. Suitable cross-linking agents include N,N'-methylene-bis-acrylamide, N,N'-diallyltartardiamide, N,N'-dihydroxyethylene-bis-acrylamide, and the like, all of which are capable of cross-linking acrylamide-type polymers by covalently bonded linkages. Such cross-linking agents, as is well-known, may be mixed with the desired monomer during or prior to polymerization to form the desired linkages. The relative proportions of monomer and of cross-linking agent may vary over a wide range, but preferably the molar ratio of monomer to cross-linking agent is from 10:1 to 50:1, sufficient to render the polymer water-insoluble.

For best results it is preferred that the polymerization be carried out in solution in a suitable solvent such as water or a mixture of water with a water-soluble organic solvent such as acetonitrile, the preferred range of concentration of monomer in the solvent being from 5 to 25% by weight.

The wound cleansing particulate composition of the present invention may be used in the same manner as other wound cleansing agents by applying directly to the wound, burn, or skin lesion a layer or mass of the particulate cross-linked polymer and allowing it to remain in place to absorb serum, pus or other fluid present. When the particles become saturated with fluid, they are removed and replaced with fresh particles of cross-linked polymer. The particles may be held in place, if desired, by any conventional bandage or dressing.

There may also be incorporated in the composition, either in the form of separate particles mixed with the cross-linked polymer particles or adsorbed or chemically bonded to the cross-linked polymer particles any conventional additive which is physiologically acceptable and non-toxic such as drugs, bactericides, or disinfectants, including such materials as fibrin or fibrin degradation products to promote angiogenesis, gelatin or collagen to complex with plasma or tissue proteins, proteolytic enzymes to debride nonviable damaged tissue, and serum albumin to protect healing tissue from excess protease.

The following specific examples are intended to illustrate the nature of the invention without acting as a limitation upon its scope.

EXAMPLE 1

A 10% by weight solution of acrylamide monomer in 0.375 molar aqueous Tris buffer (pH 8.8) was prepared containing N,N'-methylene-bis-acrylamide cross-linking agent, the molar ratio of monomer:cross-linking agent being 37:1. The solution was polymerized by adding 0.14% by weight of N,N,N',N'-tetramethylethylenediamine (TMEDA) and 5% by weight ammonium persulfate in the form of a 0.5% aqueous solution, and allowing the mixture to stand at room temperature exposed to the atmosphere. The entire solution formed a gel which was then broken into chunks and homogenized in a Waring Blender, and washed extensively with distilled water to remove salts and unreacted monomer. The product was then dried at 125° C., ground in a mortar and pestle, and sieved to obtain particles having a diameter less than 0.3 mm.

In a second embodiment, the same procedure was followed except that the concentration of acrylamide monomer in solution was 12.5% by weight.

The capacity for fluid absorption of the polymer particles thus prepared was determined by placing a 50 mg sample of each in a microfilter tube fitted with 1.2 μm cellulose acetate membrane and wetting the sample with 1 ml of Hank's balanced salt solution (pH 7.2). After incubation of the tubes at 37° C. for 4 hours, the particles in each tube were sedimented by centrifugation and the supernatant decanted. The ratio of the weight of fluid absorbed to the weight of dry polymer (duplicate determinations) was as follows:

| Sample | Wt. Ratio of Absorbed Fluid to Dry Polymer |
| --- | --- |
| 10% Monomer solution polymerization | 6.03; 5.95 |
| 12.5% Monomer solution polymerization | 6.80; 7.54 |

In contrast a particulate wound cleansing agent commercially available under the name "Debrisan" (Pharmacia) and reported to be dextran cross-linked with epichlorohydrin, when tested under the same conditions exhibited an absorbed fluid ratio of 2.14 and 2.13.

EXAMPLES 2–5

There were dissolved in three different 60 ml aliquots of a 20% by volume aqueous solution of acetonitrile in separate containers the following monomers in the specified amounts:
Acrylamide: 6.0 grams
Methacrylamide: 7.18 grams
N-isopropylacrylamide: 9.55 grams
To each solution there was added 324 mg of N,N'-methylene-bis-acrylamide cross-linking agent to provide a molar ratio of monomer to cross-linking agent of 40:1. After deaeration of each solution by bubbling helium through it, there was added to each 1 ml of a 0.003 molar solution of azobisisobutyronitrile initiator in an 80:20 water-acetonitrile solution. The containers were then sealed and shaken for 14 hours at 60° C., after which the polymer gels were removed from the containers, passed through a Waring Blender, washed with water, with a 50:50 methanol:water mixture, and again with water.

The samples were then dried at 125° C., ground and sieved to provide particles having a maximum diameter of 0.3 mm. The fluid uptake of each sample was then measured as described in Example 1 above with the following results:

| Sample | Wt. Ratio of Absorbed Fluid to Dry Polymer |
| --- | --- |
| Polyacrylamide | 13.6; 13.4 |
| Polymethacrylamide | 2.47; 2.47 |
| Poly(N—isopropyl-acrylamide) | 9.33; 8.99 |

Samples of Debrisan particles tested under the same conditions exhibited a fluid absorption ratio of 2.22; 2.25. The polymer particles were found upon testing to have little or no effect upon prothrombin time, upon activated partial thromboplastin time, or upon protease activity of normal human citrated plasma. When exposed to Hank's balanced salt solution containing 2.0–2.5% by weight of bovine serum albumin, the particles of cross-linked polymethacrylamide and poly(N-isopropylacrylamide) exhibited remarkably high capacity for absorbance of protein, more than four times that of Debrisan particles tested under the same conditions; they also exhibited a bright white color when wet with whole blood or hemolyzed serum, in contrast to Debrisan particles, which became translucent and were extremely difficult to see under such conditions. The cross-linked polyacrylamide particles of Example 1 also exhibited a high protein absorption capacity, at least twice that of Debrisan particles.

What is claimed is:

1. The method of cleansing, in patients in need of such cleansing, wounds and skin lesions or ulcers which comprises applying directly thereto in the absence of added organic liquid vehicle an effective amount of dry solid particles from 0.1 to 0.5 mm in diameter of a cross-linked water-insoluble polymer having the following polymer units

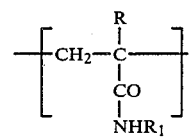

in which R is hydrogen, methyl or ethyl and $R_1$ is hydrogen, alkyl having 1 to 6 carbon atoms, or phenyl, said polymer being cross-linked with N,N'-methylene-bis-acrylamide or N,N'-diallyltartardiamide or N,N'-dihydroxyethylene-bis-acrylamide, the molar ratio of said polymer units to cross-linking agent being from 10:1 to 50:1, and
    maintaining said particles in place to absorb serum or pus.

2. The method as claimed in claim 1 in which R and $R_1$ together contain at least one carbon atom.

3. The method as claimed in claim 1 in which R is methyl.

4. The method as claimed in claim 1 in which R is hydrogen and $R_1$ is alkyl having from 1 to 6 carbon atoms.

5. The method as claimed in claim 3 in which $R_1$ is isopropyl.